(12) United States Patent
Huang

(10) Patent No.: US 10,234,443 B2
(45) Date of Patent: Mar. 19, 2019

(54) SPECTROSCOPIC TISSUE ANALYSIS APPARATUS AND METHODS

(71) Applicant: National University of Singapore, Singapore (SG)

(72) Inventor: Zhiwei Huang, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 15/911,005

(22) Filed: Mar. 2, 2018

(65) Prior Publication Data

US 2018/0252695 A1    Sep. 6, 2018

(30) Foreign Application Priority Data

Mar. 3, 2017  (SG) .............................. 10201701707S

(51) Int. Cl.
| | |
|---|---|
| *G01J 3/00* | (2006.01) |
| *G01N 33/483* | (2006.01) |
| *G01N 21/47* | (2006.01) |
| *G01N 21/31* | (2006.01) |
| *G01N 21/21* | (2006.01) |
| G01N 21/359 | (2014.01) |

(52) U.S. Cl.
CPC ......... *G01N 33/4833* (2013.01); *G01N 21/21* (2013.01); *G01N 21/31* (2013.01); *G01N 21/47* (2013.01); *G01N 21/4738* (2013.01); *G01N 21/4795* (2013.01); *G01N 21/359* (2013.01); *G01N 2021/217* (2013.01); *G01N 2021/4709* (2013.01); *G01N 2021/4792* (2013.01); *G01N 2201/129* (2013.01)

(58) Field of Classification Search
CPC . G01J 3/02; G01J 33/48; G01N 33/48; G01N 21/21; G01N 21/31; G01N 21/47
See application file for complete search history.

(56) References Cited

U.S. PATENT DOCUMENTS

2009/0119808 A1*  5/2009  Giakos .................. G01Q 60/22
                                                                        850/31

OTHER PUBLICATIONS

L. A. Torre, F. Bray, R. L. Siegel, J. Ferlay, J. Lortet-Tieulent, and A. Jemal, "Global cancer statistics, 2012," CA: a cancer journal for clinicians 65, 87-108 (2015).
N. R. o. D. Office, "Trends in Cancer Incidence in Singapore, 2010-2014," Singapore Cancer Registry Interim Annual Report, 1-56 (2015).

(Continued)

*Primary Examiner* — Abdullahi Nur
(74) *Attorney, Agent, or Firm* — JCIP; Joseph G. Chu

(57) ABSTRACT

An apparatus for spectroscopic tissue analysis is disclosed. The apparatus comprises: a light delivery system configured to direct an excitation signal on to a tissue sample; a light collection system configured to collect a backscattered signal comprising diffuse reflectance photons backscattered by the tissue sample; an imaging device; a spectrometer; an optical adaptor configured to direct a first portion of the backscattered signal to the imaging device and a second portion of the backscattered signal to the spectrometer; and an analysis system configured to apply polar decomposition to spectral image data of the tissue captured by the imaging device and the spectrometer and thereby derive polarization metrics for the tissue sample.

9 Claims, 6 Drawing Sheets
(6 of 6 Drawing Sheet(s) Filed in Color)

(56) References Cited

OTHER PUBLICATIONS

D. J. Robertson, D. A. Lieberman, S. J. Winawer, D. J. Ahnen, J. A. Baron, A. Schatzkin, A. J. Cross, A. G. Zauber, T. R. Church, and P. Lance, "Colorectal cancers soon after colonoscopy: a pooled multicohort analysis," Gut, gutjnl-2012 (2013).
M. S. Bergholt, K. Lin, J. Wang, W. Zheng, H. Xu, Q. Huang, J.-I. Ren, K. Y. Ho, M. Teh, S. Srivastava, B. Wong, K. G. Yeoh, and Z. Huang, "Simultaneous fingerprint and high-wavenumber fiber-optic Raman spectroscopy enhances real-time in vivo diagnosis of adenomatous polyps during colonoscopy," Journal of Biophotonics 9999, n/a-n/a (2015).
S. Winawer, R. Fletcher, D. Rex, J. Bond, R. Burt, J. Ferrucci, T. Ganiats, T. Levin, S. Woolf, and D. Johnson, "Colorectal cancer screening and surveillance: clinical guidelines and rationale—update based on new evidence," Gastroenterology 124, 544-560 (2003).
S. Alali, and A. Vitkin, "Polarized light imaging in biomedicine: emerging Mueller matrix methodologies for bulk tissue assessment," Journal of Biomedical Optics 20, 061104-061104 (2015).
J. Qi, M. Ye, M. Singh, N. T. Clancy, and D. S. Elson, "Narrow band 3×3 Mueller polarimetric endoscopy," Biomedical optics express 4, 2433-2449 (2013).
W. Wang, L. G. Lim, S. Srivastava, J. S. B. Yan, A. Shabbir, and Q. Liu, "Roles of linear and circular polarization properties and effect of wavelength choice on differentiation between ex vivo normal and cancerous gastric samples," Journal of biomedical optics 19, 046020-046020 (2014).
M. Sun, H. He, N. Zeng, E. Du, Y. Guo, S. Liu, J. Wu, Y. He, and H. Ma, "Characterizing the microstructures of biological tissues using Mueller matrix and transformed polarization parameters," Biomedical optics express 5, 4223-4234 (2014).
I. Ahmad, M. Ahmad, K. Khan, S. Ashraf, S. Ahmad, and M. Ikram, "Ex vivo characterization of normal and adenocarcinoma colon samples by Mueller matrix polarimetry," Journal of Biomedical Optics 20, 056012-056012 (2015).
R. S. Gurjar, V. Backman, L. T. Perelman, I. Georgakoudi, K. Badizadegan, I. Itzkan, R. R. Dasari, and M. S. Feld, "Imaging human epithelial properties with polarized light-scattering spectroscopy," Nature Medicine 7, 1245-1248 (2001).
S. G. Demos, and R. R. Alfano, "Optical polarization imaging," Applied Optics 36, 150-155 (1997).
X. Shao, W. W Zheng, and Z. Huang, "Polarized near-infrared autofluorescence imaging combined with near-infrared diffuse reflectance imaging for improving colonic cancer detection," Optics express 18, 24293-24300 (2010).
R. D. Allen, J. J Brault, and R. D. Moore, "A new method of polarization microscopic analysis I. Scanning with a birefringence detection system," The Journal of cell biology 18, 223-235 (1963).
S. B. Mehta, M. Shribak, and R. Oldenbourg, "Polarized light imaging of birefringence and diattenuation at high resolution and high sensitivity," Journal of Optics 15, 094007 (2013).
K. Sokolov, R. Drezek, K. Gossage, and R. Richards-Kortum, "Reflectance spectroscopy with polarized light: is it sensitive to cellular and nuclear morphology," Optics Express 5, 302-317 (1999).
D. S. Kliger, and J. W. Lewis, Polarized light in optics and spectroscopy (Elsevier, 2012).
M.-R. Antonelli, A. Pierangelo, T. Novikova, P. Validire, A. Benali, B. Gayet, and A. De Martino, "Mueller matrix imaging of human colon tissue for cancer diagnostics: how Monte Carlo modeling can help in the interpretation of experimental data," Optics express 18, 10200-10208 (2010).
S. L. Jacques, J. R. Roman, and K. Lee, "Imaging superficial tissues with polarized light," Lasers in surgery and medicine 26, 119-129 (2000).
X. Han, H Lui, D. I. McLean, and H. Zeng, "Near-infrared autofluorescence imaging of cutaneous melanins and human skin in vivo," Journal of biomedical optics 14, 024017-024017 (2009).
Z. Huang, H. Zeng, I. Hamzavi, A. Alajlan, E. Tan, D. I. McLean, and H. Lui, "Cutaneous melanin exhibiting fluorescence emission under near-infrared light excitation," Journal of biomedical optics 11, 034010-034010 (2006).
J. Wang, M. S. Bergholt, W. Zheng, and Z. Huang, "Development of a beveled fiber-optic confocal Raman probe for enhancing in vivo epithelial tissue Raman measurements at endoscopy," Optics letters 38, 2321-2323 (2013).
K. Lin, W. Zheng, and Z. Huang, "Integrated autofluorescence endoscopic imaging and point-wise spectroscopy for real-time in vivo tissue measurements," Journal of Biomedical Optics 15, 040507-040507-040503 (2010).
R. M. A. Azzam, "Photopolarimetric measurement of the Mueller matrix by Fourier analysis of a single detected signal," Optics Letters 2, 148-150 (1978).
D. H. Goldstein, "Mueller matrix dual-rotating retarder polarimeter," Applied optics 31, 6676-6683 (1992).
S.-Y. Lu, and R. A. Chipman, "Interpretation of Mueller matrices based on polar decomposition," JOSA A 13, 1106-1113 (1996).
J. Wang, K. Lin, W. Zheng, K. Y. Ho, M. Teh, K. G. Yeoh, and Z. Huang, "Simultaneous fingerprint and high-wavenumber fiber-optic Raman spectroscopy improves in vivo diagnosis of esophageal squamous cell carcinoma at endoscopy," Scientific reports 5 (2015).
N. Ghosh, and I. A. Vitkin, "Tissue polarimetry: concepts, challenges, applications, and outlook," Journal of biomedical optics 16, 110801-11080129 (2011).
M. Fleming, S. Ravula, S. F. Tatishchev, and H. L. Wang, "Colorectal carcinoma: Pathologic aspects," Journal of gastrointestinal oncology 3, 153 (2012).
J. M. Bueno, "Measurement of parameters of polarization in the living human eye using imaging polarimetry," Vision Research 40, 3791-3799 (2000).
J. G. Bayly, V. B. Kartha, and W. H. Stevens, "The absorption spectra of liquid phase $H_2O$, HDO and $D_2O$ from 0•7 μm to 10 μm," Infrared Physics 3, 211-222 (1963).
R. Wolthuis, M. van Aken, K. Fountas, J. S. Robinson Jr, H. A. Bruining, and G. J. Puppets, "Determination of water concentration in brain tissue by Raman spectroscopy," Analytical chemistry 73, 3915-3920 (2001).
J. Turnay, N. Olmo, J. G. Gavilanes, and M. A. Lizarbe, "Collagen metabolism in human colon adenocarcinoma," Connective tissue research 23, 251-260 (1989).
J. Wang, K Lin, W. Zheng, K. Y. Ho, M. Teh, K. G. Yeoh, and Z. Huang, "Fiber-optic Raman spectroscopy for in vivo diagnosis of gastric dysplasia," Faraday Discussions (2015).

* cited by examiner

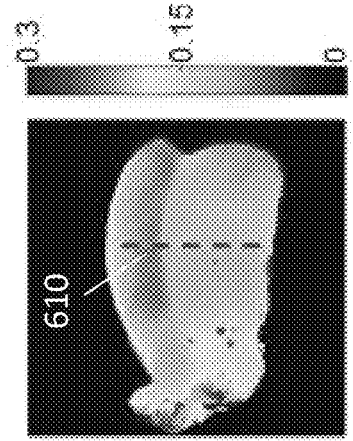
FIG. 6a
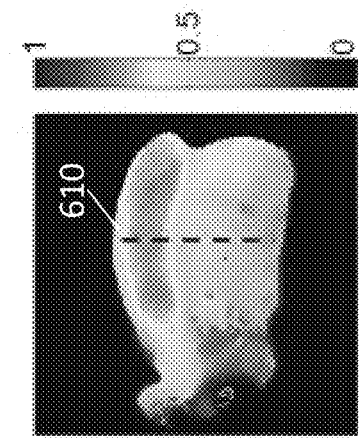
FIG. 6b
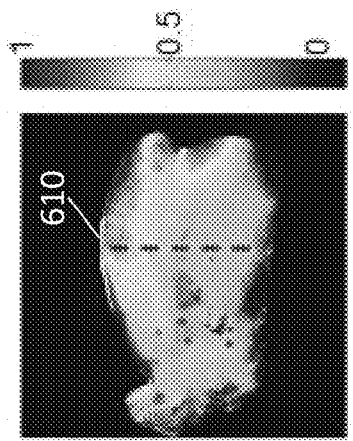
FIG. 6c
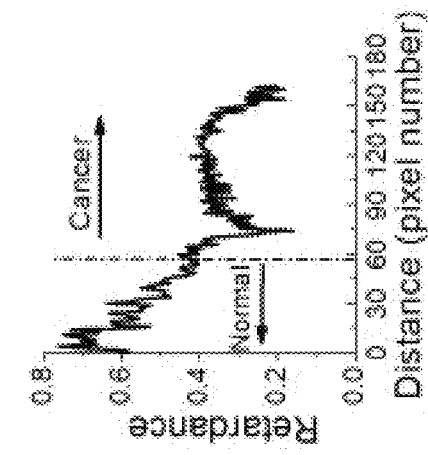
FIG. 6d
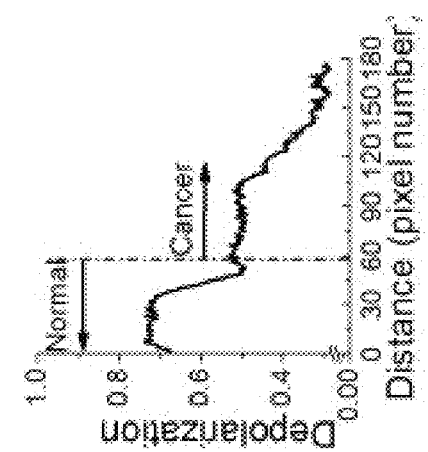
FIG. 6e
FIG. 6f

SPECTROSCOPIC TISSUE ANALYSIS APPARATUS AND METHODS

RELATED APPLICATION

This application claims priority to, and the benefit of, the Singapore patent application No. 10201701707S filed on Mar. 3, 2017, the content of which is incorporated in its entirety herein.

FIELD

The present disclosure relates to spectroscopic tissue analysis and in particular to Mueller Matrix imaging and spectroscopy in the detection and diagnosis of cancer.

BACKGROUND

Colorectal cancer (CRC) is the third most commonly diagnosed cancer in males and the second in females worldwide, with an estimated 1.4 million cases and 693,900 deaths occurring in 2012 [1]. In Singapore, CRC has become the most frequent cancer with a total of 9,324 new cases diagnosed from 2010-2014 [2]. Current routine screening of CRC uses white light reflectance (WLR) colonoscopy which may reduce CRC incidence and mortality [3]. However, some individuals are still diagnosed with CRC despite recent colonoscopy [3]. This is probably because conventional WLR colonoscopy heavily relies on the visualization of gross mucosal features associated with neoplastic transformation [4]. Subtle tissue changes may not be apparent, limiting its diagnostic accuracy. Consequently, existing diagnostic guidelines recommend extensive but random biopsy samplings during colonoscopic inspections of patients [5], followed by the microscopic examination which is highly subjective and depends heavily on the experiences of the pathologists. Overall, the current approach for colonic tissue diagnosis is clinically labor intensive and a burden to the patients. There is a need to develop advanced optical diagnostic techniques for objective diagnosis and characterization of colonic tissue.

In the past few decades, polarized light imaging/spectroscopy has been comprehensively investigated for tissue diagnosis [6-17]. Polarized light implementation offers several compelling advantages: (1) surface and beneath-the-surface detection of biological tissue taken from the tissue depolarization [12, 16]; (2) tissue anisotropy analyzed through the tissue diattenuation and retardance [14, 15]; (3) enhanced tissue diagnosis through the combination of complementary depolarization, diattenuation and retardance of the tissues [8, 10]. Among the various polarized light imaging/spectroscopy techniques developed [6-15, 18], Mueller Matrix polarimetry is capable of measuring the complete polarimetric transfer function [6-10], known as Mueller matrix, of the bulk biological tissues which are optically inhomogeneous, birefringent, and absorbing media [19]. Currently, biomedical Mueller Matrix polarimetry is mostly centered on the use of short visible wavelengths of illumination light that has a limited penetration depth and cannot detect lesions in deeper areas [8-10]. The near-infrared (NIR) light, on the other hand, penetrates much deeper into the tissue, and it is well-suited for deep tissue diagnosis [13, 20-22]. Further, the reported Mueller Matrix polarimetries are acquiring either the images [7-9] or the optical spectra [10] of the biological tissues alone.

SUMMARY OF THE INVENTION

The present disclosure relates to a unique integrated Mueller Matrix NIR imaging and point-wise Mueller Matrix spectroscopy system for colonic tissue diagnosis and characterization. Point-wise Mueller Matrix diffuse reflectance (DR) spectra are acquired from any suspicious areas as indicated by the Mueller Matrix images. Polar decomposition algorithms are employed on the acquired Mueller Matrix images/spectra to derive three polarization metrics including depolarization, diattenuation and retardance. Partial least squares discriminant analysis (PLS-DA) and leave-one tissue site-out, cross validation (LOSCV) were implemented on the derived spectroscopic polarization metrics (i.e., depolarization, diattenuation and retardance) to develop robust spectral diagnostic models for the differentiation between cancerous and normal colonic tissues.

According to a first aspect of the present disclosure, an apparatus for spectroscopic tissue analysis is provided. The apparatus comprises: a light delivery system configured to direct an excitation signal on to a tissue sample; a light collection system configured to collect a backscattered signal comprising diffuse reflectance photons backscattered by the tissue sample; an imaging device; a spectrometer; an optical adaptor configured to direct a first portion of the backscattered signal to the imaging device and a second portion of the backscattered signal to the spectrometer; and an analysis system configured to apply polar decomposition to spectral image data of the tissue captured by the imaging device and the spectrometer and thereby derive polarization metrics for the tissue sample.

In an embodiment, the analysis system is configured to use the polarization metrics to characterize the tissue.

In an embodiment, the derived polarization metrics comprise depolarization; and/or diattenuation and/or retardance.

In an embodiment, the analysis system is configured to apply polar decomposition to the spectral image data by expressing a Mueller matrix as a product of three matrices, the three matrices being a diattenuation matrix, a depolarization matrix and a retardance matrix.

In an embodiment, the tissue sample comprises colonic tissue.

In an embodiment, the analysis system is configured to identify cancerous tissue.

In an embodiment, the analysis system is configured to characterize the tissue by applying partial least squares discriminant analysis and leave-one tissue site-out, cross validation to the polarization metrics.

In an embodiment, the optical adapter comprises a glass plate having portion coated with a mirror.

In an embodiment, the optical adapter is configured such that the first portion of the backscattered signal is transmitted by the glass plate and the second portion of the backscattered signal is reflected by the mirror.

In an embodiment, the a backscattered signal is in the near infra-red frequency range.

According to a second aspect of the present disclosure a spectroscopic tissue analysis is provided. The method comprises: obtaining spectral image data of a tissue, the spectral image data comprising near infra-red Mueller matrix diffuse reflectance spectral data for a plurality of points of the tissue; applying polar decomposition to the spectral image data of the tissue to derive polarization metrics; and using the polarization metrics to characterize the tissue.

In an embodiment, the derived polarization metrics comprise depolarization; and/or diattenuation and/or retardance.

In an embodiment, applying polar decomposition to the spectral image data comprises expressing a Mueller matrix as a product of three matrices, the three matrices being a diattenuation matrix, a depolarization matrix and a retardance matrix.

In an embodiment, the tissue is colonic tissue.

In an embodiment, the polarization metrics to characterize the tissue comprises identifying cancerous tissue.

In an embodiment, the polarization metrics to characterize the tissue comprises applying partial least squares discriminant analysis and leave-one tissue site-out, cross validation to the polarization metrics.

BRIEF DESCRIPTION OF THE DRAWINGS

This patent application file contains at least one drawing executed in color. Copies of this patent application publication with color drawings will be provided by the Office upon request and payment of the necessary fee.

In the following, embodiments of the present invention will be described as non-limiting examples with reference to the accompanying drawings in which:

FIGS. 6a to 6c show processed diattenuation, depolarization and retardance images respectively;

FIGS. 6d to 6f show intensity profiles across the images shown in FIGS. 6a to 6c respectively;

DETAILED DESCRIPTION

Figure 1:
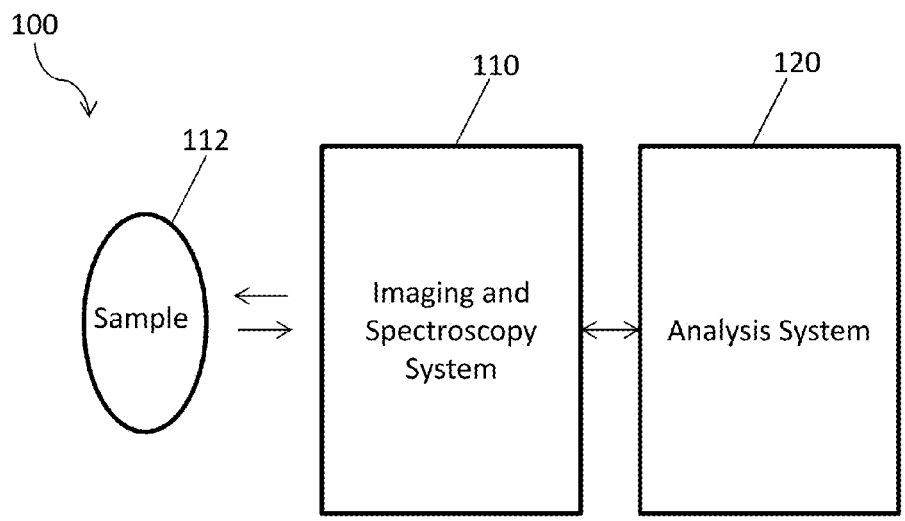
FIG. 1 is a block diagram showing an apparatus for analyzing tissue according to an embodiment of the present invention.

FIG. 1 is a block diagram showing an apparatus for analyzing tissue according to an embodiment of the present invention. The apparatus 100 comprises an imaging and spectroscopy system 110 and an analysis system 120. The imaging and spectroscopy system 110 emits light, which is incident on a sample 112. Light backscattered by the sample 112 is received by the imaging and spectroscopy system 110, which carries out Mueller matrix imaging and point wise Mueller matrix spectroscopy. The analysis system 120 carries out analysis on the output generated by the imaging and spectroscopy system 110.

The imaging and spectroscopy system 110 may be implemented as described below with reference to FIG. 2. In some embodiments, the imaging and spectroscopy system 110 may comprise a probe such as an endoscope for diagnosis and detection of malignant lesions during a colonic endoscopy procedure. In other embodiments, the imaging and spectroscopy system 110 is arranged to analyze tissue samples extracted during a biopsy procedure.

The analysis system 120 may be implemented as a general purpose computer having a processor which runs a computer program to carry out analysis of the output of the imaging and spectroscopy system 110 as described in more detail below.

Figure 2:
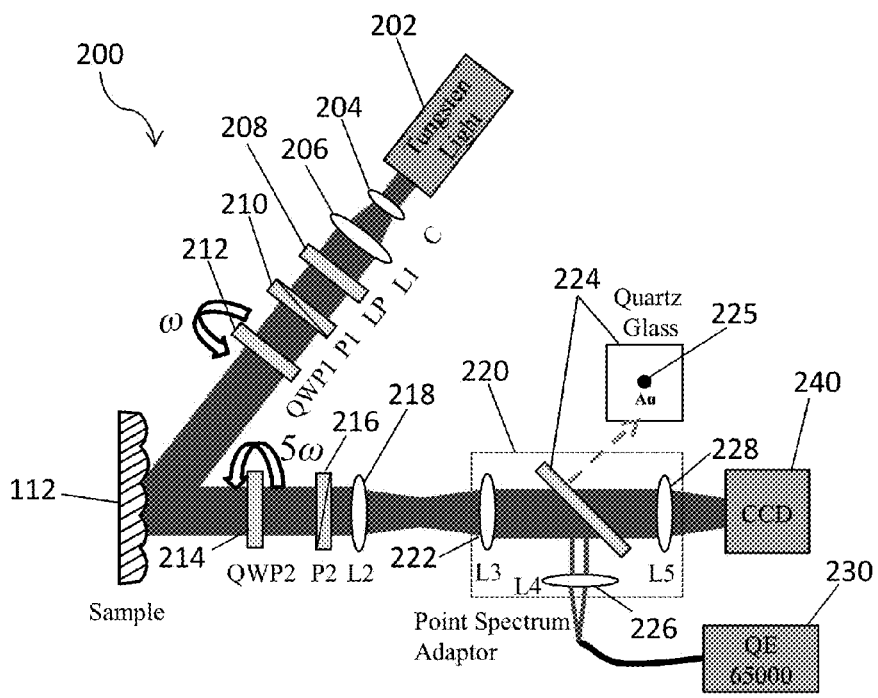
FIG. 2 shows a schematic of the imaging and spectroscopy system of an embodiment of the present invention.

FIG. 2 shows a schematic of the imaging and spectroscopy system of an embodiment of the present invention. The imaging and spectroscopy system 200 shown in FIG. 2 is an integrated Mueller matrix near infra-red (NIR) imaging and point-wise diffuse reflectance (DR) spectroscopy system developed for tissue measurements.

The light from a tungsten halogen lamp 202 (HL-2000, Ocean Optics Inc., Dunedin, Fla.) is coupled into an optical fiber and passes through a beam expander comprising a collimator (C) 204 and a lens (L1) 206, the light then passes through a long-pass filter (LP) 208 and a polarizer (LP-NIR100-MP2, Thorlabs, Newton, N.J.) (P1) 210 and, and a quarter waveplate (AQWP10M-980, Thorlabs, Newton, N.J.) (QWP1) 212.

Following the quarter waveplate 212, the light is incident on the tissue sample 112. The NIR diffuse reflectance photons backscattered from the tissue sample 112 pass through a quarter waveplate (AQWP10M-980, Thorlabs, Newton, N.J.) (QWP2) 214, a polarizer (LPNIR100-MP2, Thorlabs, Newton, N.J.) (P2) 216, a collection lens (L2) 218, and a specially designed point spectrum optical adaptor 220 [23] before they are collected by a CCD camera (Pixis 1024, Princeton Instruments, Trenton, N.J.) 240.

The customized point spectrum optical adaptor 220 comprises three lenses (f=50 mm) (L3, L4 and L5) 222, 226 & 228, a thin quartz glass plate (25×25×1 mm$^3$) 224 coated with a gold mirror 225 (diameter of 100 μm, reflection of ~99% in 850-1100 nm) and a 2-D motorized translational stage (travel range: 13 mm, 8MT184-13, Standa Inc., Lithuania) (not shown in FIG. 2). During each tissue measurement, a small portion of the backscattered light was reflected by the point spectrum optical adaptor 220 and collected by a spectrometer 230 (QE65000, Ocean Optics Inc., Dunedin, Fla.) for tissue spectroscopic analysis [23].

Figure 3:
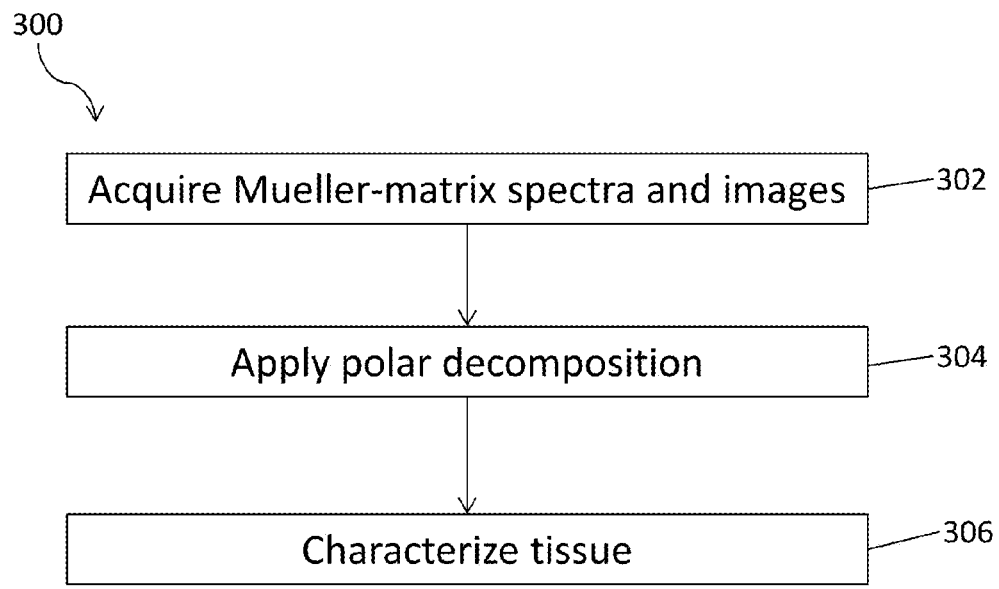
FIG. 3 is a flowchart showing a method of spectroscopic tissue analysis according to an embodiment of the present invention.

FIG. 3 is a flowchart showing a method of spectroscopic tissue analysis according to an embodiment of the present invention. The method 300 may be carried out by the apparatus 100 shown in FIG. 1.

In step 302, the Imaging and Spectroscopy System 110 acquires Mueller-matrix spectra and images of the sample. To acquire the 4 by 4 Mueller Matrix DR images/spectra, the fast axis of the polarizers (P1, P2) 210 & 216 is fixed while the quarter waveplates (QWP1, QWP2) 212 & 214 were rotating with a fixed speed ratio of 1:5. The detected intensity was Fourier modulated as [24, 25]:

$$I = a_0 + \sum_{n=1}^{12} (a_n \cos nwt + b_n \sin nwt)$$

Where ω is the rotation speed of QWP1, t is the exposure time of the camera, and $a_0$, $a_n$, $b_n$ are the Fourier coefficients which can be measured through the detected intensity I. The relationship between the 25 Fourier coefficients and the 16 Mueller Matrix elements can be found in [25]. With the integrated NIR Mueller Matrix imaging and point-wise spectroscopy system developed, a set of 25 Mueller Matrix images/spectra can be acquired for colonic tissues in tandem within 5 s when the incident optical power on sample surface is ~2 mW, and the 4 by 4 Mueller Matrix imaging/point-wise spectroscopy is achieved [24, 25]. Further automatic motorization of the small gold mirror coated on the quartz plate together with the point-wise spectral measurement module enables a rapid movement of the dark spot (of 0.2 mm in diameter due to the reflection of gold mirror in the point spectrum optical adapter) on the Mueller Matrix image to any spot of the imaged tissue of interest, and the subsequent 4 by 4 Mueller Matrix point-wise spectroscopy can be realized within 1 s.

In step 304, the analysis system 120 applies polar decomposition to the Mueller-matrix spectra and images to derive polarization metrics. To derive the colonic tissue polarization metrics (i.e., diattenuation D, depolarization Δ, and retardance R), polar decomposition [26] was implemented on the 4 by 4 Mueller Matrix images/spectra acquired with the system developed. Briefly, the tissue Mueller Matrix M is expressed as the product of three 4 by 4 matrices: the diattenuation matrix ($M_D$), the depolarization matrix ($M_\Delta$), and the retardance matrix ($M_R$) [26]:

$$M = M_\Delta M_R M_D$$

The diattenuation D, depolarization Δ, and retardance R can be determined as follows [26]:

$$D = \frac{1}{m_{11}} \sqrt{m_{12}^2 + m_{13}^2 + m_{14}^2}$$

$$\Delta = 1 - \frac{|\text{trace}(M_\Delta - 1)|}{3}$$

$$R = \cos^{-1}\left[\frac{\text{trace}(M_R)}{2} - 1\right]$$

Where ($m_{11}, m_{12}, m_{13}, m_{14}$) represent the elements of first row of the tissue Mueller Matrix M. To validate the performances of the system developed, the NIR Mueller Matrix spectra of a half waveplate and a quarter waveplate were measured and decomposed. The differences between the measured retardance and that provided by the manufacturer is less than 3%, confirming the robustness of the system developed.

In step 306, the analysis system 120 uses the derived polarization metrics to characterize the tissue sample. The unpaired two-sided Student's t-test was used to evaluate the decomposed Mueller Matrix spectroscopic differences between cancer and normal colonic tissues [27]. Partial least squares (PLS)-discriminant analysis (DA) was applied on the derived spectroscopic polarization metrics for developing spectral diagnosis models [27]. Leave-one-tissue site out, cross-validation was further used to assess and optimize the PLS-DA model complexity, while reducing the risk of over-fitting. The above multivariate statistical analysis was performed using in-house written scripts in the Matlab programming environment (Mathworks. Inc., Natick, Mass.).

The analysis of colonic tissue specimens using the systems and methods according to embodiments of the present invention will now be discussed. A total of 30 paired (i.e., normal vs cancer) colonic tissue specimens (average size of ~6×3×3 $mm^3$) were collected from 30 patients (18 men and 12 women with a mean age of 56) who underwent partial colectomy or surgical resections with clinically suspicious lesions or histopathologically proven malignancies in the colon. All patients preoperatively signed an informed consent permitting the investigative use of the tissue, and this study was approved by the Institutional Review Board (IRB) of the National Healthcare Group (NHG) of Singapore. Immediately after surgical resections, the tissue specimens were immersed in physiological saline solution and sent to the Laboratory for NIR Mueller Matrix imaging and point-wise spectroscopy measurements.

Figure 4:
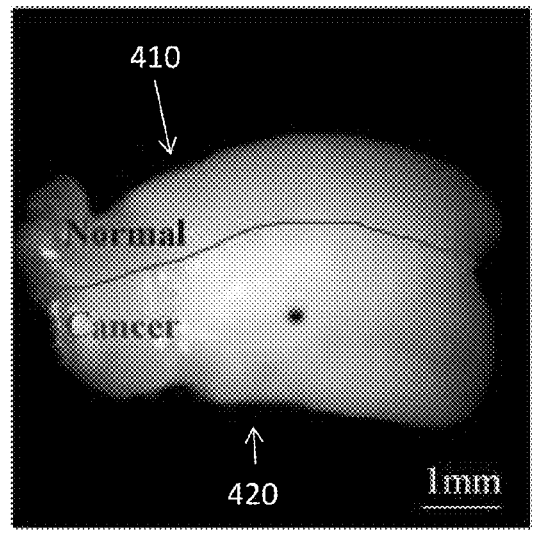
FIG. 4 shows a NIR diffuse reflectance image of a paired colonic tissue sample.

FIG. 4 shows a NIR diffuse reflectance image of a paired colonic tissue sample. The paired tissue specimens from each patient were placed on a standard glass slide (26×76× 1.2 $mm^3$) (cancer tissue 420 was placed at the bottom part of the slide while the normal one 410 was placed at upper part of the slide) for NIR imaging measurements. After the NIR imaging acquisitions, the tissue specimens were fixed in 10% formalin solution and then submitted back to the hospital for histopathological examinations. The histopathological examinations confirmed that 30 tissue specimens were normal, and 30 tissue specimens were cancer (moderately differentiated adenocarcinoma).

With the integrated NIR Mueller Matrix imaging and point-wise spectroscopy system developed, 4 by 4 NIR Mueller Matrix images of 30 paired colonic tissues were acquired.

Figure 5:
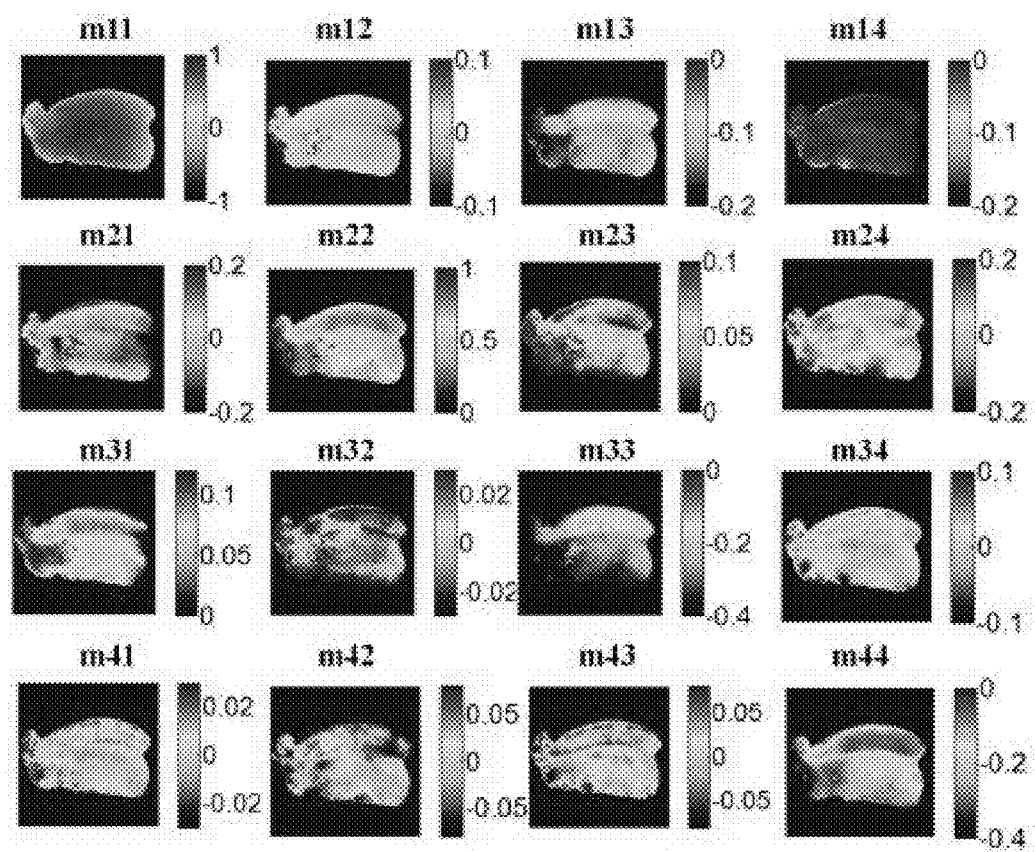
FIG. 5 shows representative normalized Muller matrix images of paired colonic tissue samples.

FIG. 5 shows representative normalized Muller matrix images of the paired (normal vs. cancer) colonic tissue samples as confirmed by histological examinations. All the Mueller matrix elements (except $m_{11}$) are normalized by $m_{11}$. It is observed from FIG. 5 that the paired colonic tissue samples have both diagonal and non-diagonal elements (i.e., $m_{34}$), and the $m_{22}$ and $m_{33}$ elements are essentially different. The results in FIG. 5 demonstrate that the colonic tissue is accompanied with characteristic features of anisotropic media. Moreover, it is also found that the colonic cancer is associated with increased value of $m_{22}$ and $m_{33}$ elements, indicating a lower depolarization power for colonic cancer.

Using the results shown in FIG. 5, quantitative biophysical polarization metrics (i.e., diattenuation, depolarization, and retardance) were further derived using the polar decomposition algorithms. These metrics are illustrated in FIGS. 6a to 6f.

FIGS. 6a to 6c show processed diattenuation, depolarization and retardance images respectively. FIGS. 6d to 6f show intensity profiles across the images shown in FIGS. 6a to 6c respectively.

As shown in FIG. 6a, the diattenuation of colonic cancer sample is higher than that of normal colonic tissue. The diattenuation profile shown in FIG. 6d along the line 610 drawn around the center of the field of view (FOV) of diattenuation image confirms the significantly increased diattenuation for the colon cancer. It is noted that biomolecules such as amino acids, proteins and nucleic acids exhibit diattenuation effects [28]. The higher magnitude observed for the diattenuation of cancerous tissue compared to normal tissue may be due to the enlarged nuclei and increased concentrations of chromatin (hence, nucleic acids) during colonic cancer development [29], which led to the increase in diattenuation effects in colonic cancer. Further, the cancerous colon sample at the bottom clearly exhibits less depolarization effects as can be seen in FIGS. 6b and 6e. The decreased depolarization effects of cancer tissue can be attributed by the multiple scattering effects of polarized incident light in the bulk colonic tissue, originating from variations in the refractive indices of tissue microstructures [18]. Since an increase in cellular and nuclear sizes arises is accompanied with high cellular density and vascularization during cancer progression, an enhancement in anisotropic or Mie (directionally dependent) scattering of light in cancerous tissue causes less depolarizing effects as compared to isotropic or Rayleigh scattering in normal tissue [18, 29]. Besides, the retardance image shown in FIG. 6c shows the colonic tissue retardance distribution with lower retardance values for colonic cancer as can be seen in FIG. 6f. Overall, the results in FIGS. 6a to 6f demonstrate the potential of NIR Mueller Matrix imaging for the characterization and diagnosis of colonic cancer.

By rapidly moving the gold mirror within the optical adaptor, 60 further sets of spectroscopic Mueller Matrix spectra from the suspicious regions were acquired. In the acquired sets (normal: n=30; cancer: n=30) the variation of the Mueller Matrix elements with wavelength was investigated.

Figure 7:
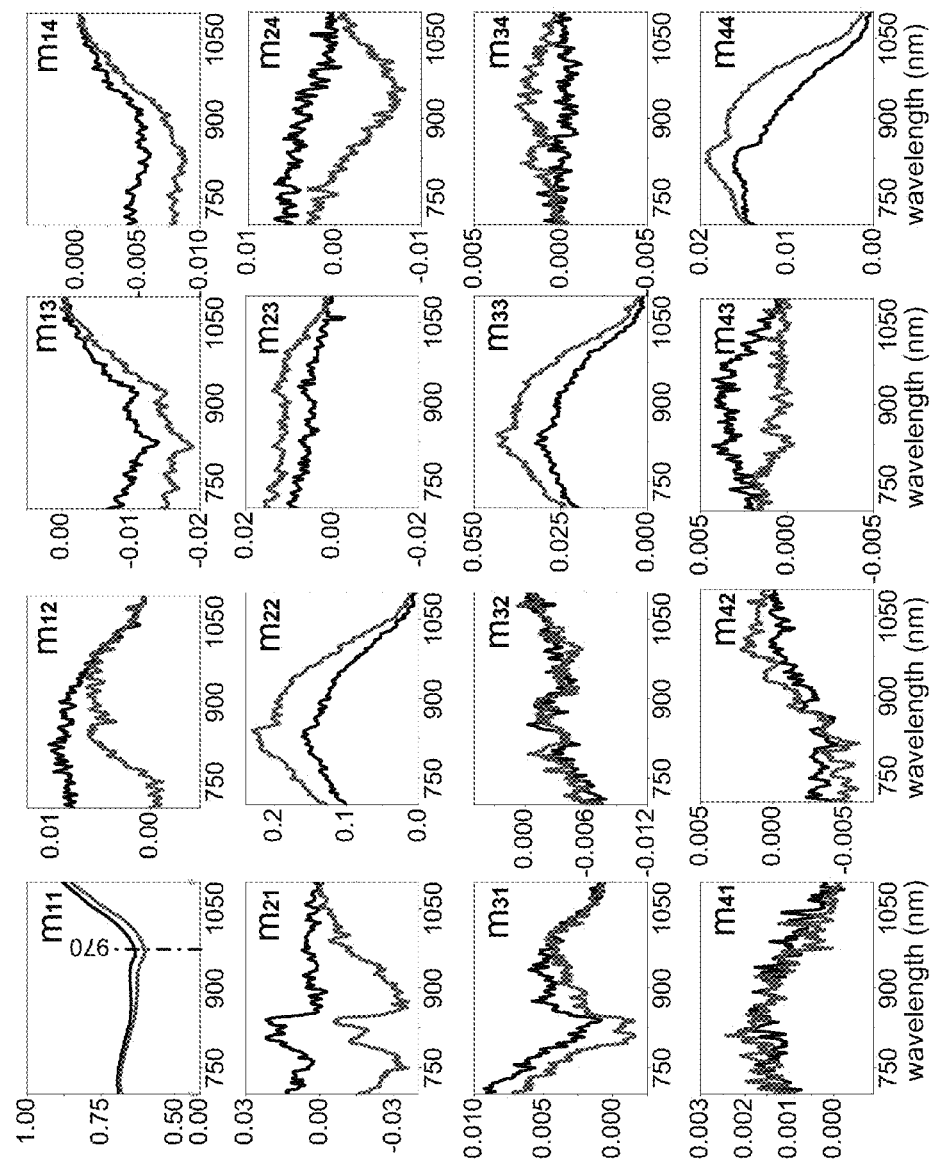
FIG. 7 shows representative 4 by 4 NIR Muller matrix DR spectra recorded of normal and cancerous colonic tissue.

FIG. 7 shows representative 4 by 4 NIR Muller matrix DR spectra recorded of normal and cancerous colonic tissue. The data for normal tissue is shown in black and the data for cancerous tissue is shown in black. FIG. 7 shows the typical 4 by 4 Mueller Matrix spectra acquired from the histopathologically confirmed normal and cancerous colonic tissues. Clearly, it was found that non-diagonal spectroscopic Mueller Matrix elements (i.e., $m_{34}$), and the values of $m_{22}$ and $m_{33}$ are different, reconfirming the anisotropy of the colonic tissues. One notes that $m_{11}$ generally represents the overall diffuse reflectance spectra of colonic tissue when unpolarized light is used [30]. Prominent water absorption valley can be observed at 970 nm [31] for both normal and cancer colonic tissues. Besides, the water absorption valley is more obvious on the cancer tissue spot than on the normal one, indicating increased water content for the colonic tissues. The increased water for the cancerous colonic tissue has been observed by using the other techniques (i.e., Raman spectroscopy [4]) and in the other soft tissues as well (i.e., esophagus [27], and brain [32]).

Figure 8C:
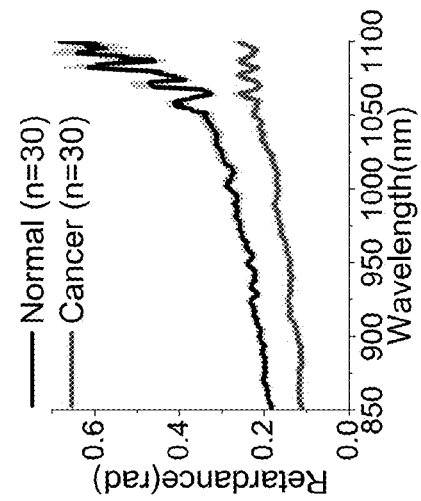
FIGS. 8a to 8c show spectral variation of the calculated metrics for normal and cancerous tissue.
Figure 8B:
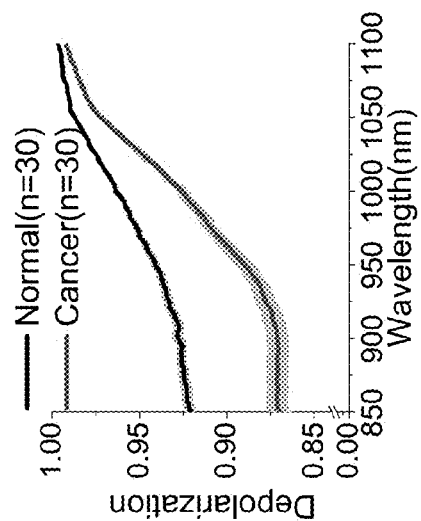
Figure 8A:
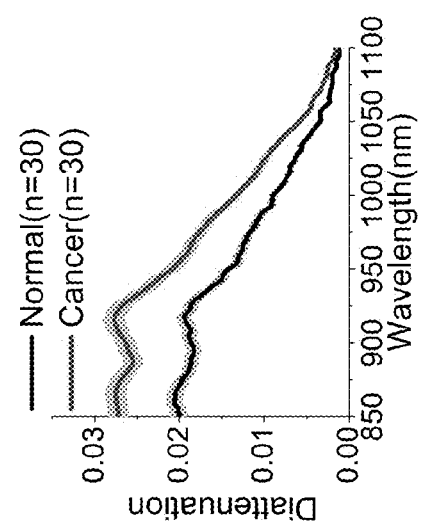

FIGS. 8a to 8c show spectral variation of the calculated metrics for normal and cancerous tissue. FIG. 8a shows diattenuation±1 standard error (SE) (shaded area), FIG. 8b shows retardance±1 SE and FIG. 8c shows depolarization±1 SE, for the paired (normal (n=30) vs cancer (n=30)) colonic tissue samples.

As consistent with the decomposed Mueller Matrix images shown in FIGS. 5a, 5b, 5d and 5e, we found a significantly (p<0.01) increased diattenuation while the depolarization was reduced associated with the colonic cancer, demonstrating the potential of the Mueller Matrix spectroscopy for colon cancer diagnosis. Remarkably, the decomposed retardance spectra show a clear decrease for the colonic cancer. This phenomenon is likely caused by the decreased collagen content in the colon cancer tissues [33] if one notes that the retardance effects are mainly attributed by the anisotropic orientation of collagen fibers in the concentric lamina propria and submucosa layers of the cross-section of a colon wall [10].

To develop robust multivariate spectral diagnostic algorithms for the detection of colonic cancer, PLS-DA and LOSCV were further implemented on the 3 derived spectroscopic polarimetric metrics. The results of this analysis are shown in Table 1 below:

TABLE 1

Diagnostic results of colonic cancer by using Mueller Matrix DR spectroscopy together with PLS-DA and LOSCV

|  | Sensitivity (%) | Specificity (%) | Accuracy (%) |
| --- | --- | --- | --- |
| Diattentuation (D) | 83.3 | 96.7 | 90.0 |
| Depolarization (Δ) | 93.3 | 90.0 | 91.7 |
| Retardance (R) | 80.0 | 80.0 | 80.0 |
| Combined D, Δ and R | 93.3 | 96.7 | 95.0 |

The PLS-DA and LOSCV analysis shows that the colon cancer was identified with accuracy of 90.0%, 91.7%, and 80.0% respectively by using diattenuation, depolarization, and retardance metrics. The combination of the three polarization metrics with majority voting [34] provides an enhanced colonic cancer detection with an accuracy of 95.0% (sensitivity of 93.3%, and specificity of 96.7%), superior to using either of the three polarization metrics alone.

In summary, a unique integrated Mueller Matrix NIR imaging and Mueller Matrix point-wise spectroscopy system was developed for tissue characterization and diagnosis. Point-wise Mueller Matrix spectra can be acquired under the guidance of the Mueller Matrix imaging. Significantly increased diattenuation while significantly reduced depolarization and retardance effects were observed associated with the colonic cancer. Using the decomposed spectroscopic polarimetric metrics (i.e., diattenuation, depolarization, and retardance), colonic cancer can be detected with high accuracy (~95%). This work demonstrates that Mueller Matrix NIR imaging and point-wise spectroscopy system may open a new way for the enhanced detection and diagnosis at endoscopy.

Whilst the foregoing description has described exemplary embodiments, it will be understood by those skilled in the art that many variations of the embodiments can be made within the scope and spirit of the present invention.

For example, the excitation light delivery may be minimized, wavelengths and polarization may be controlled with polarization maintaining fibers, acousto-optical tunable filters (AOTFs) and liquid crystal lenses which can be introduced into the Mueller-Matrix imaging and spectroscopy system.

REFERENCES

1. L. A. Torre, F. Bray, R. L. Siegel, J. Ferlay, J. Lortet☐Tieulent, and A. Jemal, "Global cancer statistics, 2012," CA: a cancer journal for clinicians 65, 87-108 (2015).
2. N. R. o. D. Office, "Trends in Cancer Incidence in Singapore, 2010-2014," Singapore Cancer Registry Interim Annual Report, 1-56 (2015).
3. D. J. Robertson, D. A. Lieberman, S. J. Winawer, D. J. Ahnen, J. A. Baron, A. Schatzkin, A. J. Cross, A. G. Zauber, T. R. Church, and P. Lance, "Colorectal cancers soon after colonoscopy: a pooled multicohort analysis," Gut, gutjnl-2012 (2013).
4. M. S. Bergholt, K. Lin, J. Wang, W. Zheng, H. Xu, Q. Huang, J.-I. Ren, K. Y. Ho, M. Teh, S. Srivastava, B. Wong, K. G. Yeoh, and Z. Huang, "Simultaneous fingerprint and high-wavenumber fiber-optic Raman spectroscopy enhances real-time in vivo diagnosis of adenomatous polyps during colonoscopy," Journal of Biophotonics 9999, n/a-n/a (2015).
5. S. Winawer, R. Fletcher, D. Rex, J. Bond, R. Burt, J. Ferrucci, T. Ganiats, T. Levin, S. Woolf, and D. Johnson, "Colorectal cancer screening and surveillance: clinical guidelines and rationale—update based on new evidence," Gastroenterology 124, 544-560 (2003).
6. S. Alali, and A. Vitkin, "Polarized light imaging in biomedicine: emerging Mueller matrix methodologies for bulk tissue assessment," Journal of Biomedical Optics 20, 061104-061104 (2015).
7. J. Qi, M. Ye, M. Singh, N. T. Clancy, and D. S. Elson, "Narrow band 3×3 Mueller polarimetric endoscopy," Biomedical optics express 4, 2433-2449 (2013).
8. W. Wang, L. G. Lim, S. Srivastava, J. S. B. Yan, A. Shabbir, and Q. Liu, "Roles of linear and circular polarization properties and effect of wavelength choice on differentiation between ex vivo normal and cancerous gastric samples," Journal of biomedical optics 19, 046020-046020 (2014).

9. M. Sun, H. He, N. Zeng, E. Du, Y. Guo, S. Liu, J. Wu, Y. He, and H. Ma, "Characterizing the microstructures of biological tissues using Mueller matrix and transformed polarization parameters," Biomedical optics express 5, 4223-4234 (2014).
10. I. Ahmad, M. Ahmad, K. Khan, S. Ashraf, S. Ahmad, and M. Ikram, "Ex vivo characterization of normal and adenocarcinoma colon samples by Mueller matrix polarimetry," Journal of Biomedical Optics 20, 056012-056012 (2015).
11. R. S. Gurjar, V. Backman, L. T. Perelman, I. Georgakoudi, K. Badizadegan, I. Itzkan, R. R. Dasari, and M. S. Feld, "Imaging human epithelial properties with polarized light-scattering spectroscopy," Nature Medicine 7, 1245-1248 (2001).
12. S. G. Demos, and R. R. Alfano, "Optical polarization imaging," Applied Optics 36, 150-155 (1997).
13. X. Shao, W. Zheng, and Z. Huang, "Polarized near-infrared autofluorescence imaging combined with near-infrared diffuse reflectance imaging for improving colonic cancer detection," Optics express 18, 24293-24300 (2010).
14. R. D. Allen, J. Brault, and R. D. Moore, "A new method of polarization microscopic analysis I. Scanning with a birefringence detection system," The Journal of cell biology 18, 223-235 (1963).
15. S. B. Mehta, M. Shribak, and R. Oldenbourg, "Polarized light imaging of birefringence and diattenuation at high resolution and high sensitivity," Journal of Optics 15, 094007 (2013).
16. K. Sokolov, R. Drezek, K. Gossage, and R. Richards-Kortum, "Reflectance spectroscopy with polarized light: is it sensitive to cellular and nuclear morphology," Optics Express 5, 302-317 (1999).
17. D. S. Kliger, and J. W. Lewis, Polarized light in optics and spectroscopy (Elsevier, 2012).
18. M.-R. Antonelli, A. Pierangelo, T. Novikova, P. Validire, A. Benali, B. Gayet, and A. De Martino, "Mueller matrix imaging of human colon tissue for cancer diagnostics: how Monte Carlo modeling can help in the interpretation of experimental data," Optics express 18, 10200-10208 (2010).
19. S. L. Jacques, J. R. Roman, and K. Lee, "Imaging superficial tissues with polarized light," Lasers in surgery and medicine 26, 119-129 (2000).
20. X. Han, H. Lui, D. I. McLean, and H. Zeng, "Near-infrared autofluorescence imaging of cutaneous melanins and human skin in vivo," Journal of biomedical optics 14, 024017-024017 (2009).
21. Z. Huang, H. Zeng, I. Hamzavi, A. Alajlan, E. Tan, D. I. McLean, and H. Lui, "Cutaneous melanin exhibiting fluorescence emission under near-infrared light excitation," Journal of biomedical optics 11, 034010-034010 (2006).
22. J. Wang, M. S. Bergholt, W. Zheng, and Z. Huang, "Development of a beveled fiber-optic confocal Raman probe for enhancing in vivo epithelial tissue Raman measurements at endoscopy," Optics letters 38, 2321-2323 (2013).
23. K. Lin, W. Zheng, and Z. Huang, "Integrated autofluorescence endoscopic imaging and point-wise spectroscopy for real-time in vivo tissue measurements," Journal of Biomedical Optics 15, 040507-040507-040503 (2010).
24. R. M. A. Azzam, "Photopolarimetric measurement of the Mueller matrix by Fourier analysis of a single detected signal," Optics Letters 2, 148-150 (1978).
25. D. H. Goldstein, "Mueller matrix dual-rotating retarder polarimeter," Applied optics 31, 6676-6683 (1992).
26. S.-Y. Lu, and R. A. Chipman, "Interpretation of Mueller matrices based on polar decomposition," JOSA A 13, 1106-1113 (1996).
27. J. Wang, K. Lin, W. Zheng, K. Y. Ho, M. Teh, K. G. Yeoh, and Z. Huang, "Simultaneous fingerprint and high-wavenumber fiber-optic Raman spectroscopy improves in vivo diagnosis of esophageal squamous cell carcinoma at endoscopy," Scientific reports 5 (2015).
28. N. Ghosh, and I. A. Vitkin, "Tissue polarimetry: concepts, challenges, applications, and outlook," Journal of biomedical optics 16, 110801-11080129 (2011).
29. M. Fleming, S. Ravula, S. F. Tatishchev, and H. L. Wang, "Colorectal carcinoma: Pathologic aspects," Journal of gastrointestinal oncology 3, 153 (2012).
30. J. M. Bueno, "Measurement of parameters of polarization in the living human eye using imaging polarimetry," Vision Research 40, 3791-3799 (2000).
31. J. G. Bayly, V. B. Kartha, and W. H. Stevens, "The absorption spectra of liquid phase H2O, HDO and D2O from 0·7 μm to 10 μm," Infrared Physics 3, 211-222 (1963).
32. R. Wolthuis, M. van Aken, K. Fountas, J. S. Robinson Jr, H. A. Bruining, and G. J. Puppels, "Determination of water concentration in brain tissue by Raman spectroscopy," Analytical chemistry 73, 3915-3920 (2001).
33. J. Turnay, N. Olmo, J. G. Gavilanes, and M. A. Lizarbe, "Collagen metabolism in human colon adenocarcinoma," Connective tissue research 23, 251-260 (1989).
34. J. Wang, K. Lin, W. Zheng, K. Y. Ho, M. Teh, K. G. Yeoh, and Z. Huang, "Fiber-optic Raman spectroscopy for in vivo diagnosis of gastric dysplasia," Faraday Discussions (2015).

The invention claimed is:

1. An apparatus for spectroscopic tissue analysis, the apparatus comprising:
   a light delivery system configured to direct an excitation signal on to a tissue sample;
   a light collection system configured to collect a backscattered signal comprising diffuse reflectance photons backscattered by the tissue sample;
   an imaging device;
   a spectrometer;
   an optical adaptor configured to direct a first portion of the backscattered signal to the imaging device and a second portion of the backscattered signal to the spectrometer; and
   an analysis system configured to apply polar decomposition to spectral image data of the tissue captured by the imaging device and the spectrometer, by expressing a Mueller matrix as a product of three matrices, the three matrices being a diattenuation matrix, a depolarization matrix and a retardance matrix, and thereby derive polarization metrics for the tissue sample.

2. An apparatus according to claim 1, wherein the analysis system is configured to use the polarization metrics to characterize the tissue.

3. An apparatus according to claim 2, wherein the analysis system is configured to identify cancerous tissue.

4. An apparatus according to claim 1, wherein the derived polarization metrics comprise depolarization; and/or diattenuation and/or retardance.

5. An apparatus according to claim 1, wherein the tissue sample comprises colonic tissue.

6. An apparatus according to claim 1, wherein the backscattered signal is in the near infra-red frequency range.

7. An apparatus for spectroscopic tissue analysis, the apparatus comprising:

a light delivery system configured to direct an excitation signal on to a tissue sample;

a light collection system configured to collect a backscattered signal comprising diffuse reflectance photons backscattered by the tissue sample;

an imaging device;

a spectrometer;

an optical adaptor configured to direct a first portion of the backscattered signal to the imaging device and a second portion of the backscattered signal to the spectrometer; and an analysis system configured to apply polar decomposition to spectral image data of tissue captured by the imaging device and the spectrometer and thereby derive polarization metrics for the tissue sample, wherein the analysis system is configured to use the polarization metrics to characterize the tissue by applying partial least squares discriminant analysis and leave-one tissue site-out, cross validation to the polarization metrics.

8. An apparatus for spectroscopic tissue analysis, the apparatus comprising:

a light delivery system configured to direct an excitation signal on to a tissue sample;

a light collection system configured to collect a backscattered signal comprising diffuse reflectance photons backscattered by the tissue sample;

an imaging device;

a spectrometer;

an optical adaptor configured to direct a first portion of the backscattered signal to the imaging device and a second portion of the backscattered signal to the spectrometer, wherein the optical adapter comprises a glass plate having portion coated with a mirror; and an analysis system configured (o apply polar decomposition to spectral image data of the tissue captured by the imaging device and the spectrometer and thereby derive polarization metrics for the tissue sample.

9. An apparatus according to claim 8, wherein the optical adapter is configured such that the first portion of the backscattered signal is transmitted by the glass plate and the second portion of the backscattered signal is reflected by the mirror.

\* \* \* \* \*